United States Patent [19]

Kaufman

[11] 4,235,781

[45] Nov. 25, 1980

[54] 6 OR 8 HALOALLYL SUBSTITUTED 7-HYDROXYCOUMARINS

[75] Inventor: Kurt D. Kaufman, Kalamazoo, Mich.

[73] Assignee: Thomas C. Elder, Inc., Hamilton, Ind.

[21] Appl. No.: 77,484

[22] Filed: Sep. 20, 1979

Related U.S. Application Data

[62] Division of Ser. No. 20,935, Mar. 15, 1979.

[51] Int. Cl.³ ............................................ C07D 311/16
[52] U.S. Cl. ............................ 260/343.44; 260/343.21
[58] Field of Search ..................................... 260/343.44

[56] References Cited

U.S. PATENT DOCUMENTS 3,243,441  3/1966  Ritter et al. ..................... 260/343.44

Primary Examiner—Henry R. Jiles
Assistant Examiner—Jane T. Fan
Attorney, Agent, or Firm—Gordon W. Hueschen

[57] ABSTRACT

α-Loweralkylfurocoumarins are produced by forming a β-haloalk-2-enyl, e.g., β-haloallyl, ether of a hydroxycoumarin having an active hydrogen in the position ortho to the hydroxy group, and heating the formed ether, preferably in dimethylaniline or like basic amine solvent. An abnormal Claisen rearrangement produces a novel o-hydroxy-(β-haloalk-2-enyl) coumarin intermediate which can be dehydrohalogenated directly without isolation to the desired α-loweralkylfurocoumarin, e.g., α-methylfurocoumarin.

12 Claims, No Drawings

6 OR 8 HALOALLYL SUBSTITUTED 7-HYDROXYCOUMARINS

This is a division of application Ser. No. 20,935, filed Mar. 15, 1979.

FIELD OF THE INVENTION AND PRIOR ART

This invention relates to a process for making α-loweralkylfurocoumarins and to novel intermediates produced therein.

Phenols can be converted to α-methylbenzofurans by a five-step process which involves O-allylation, Claisen rearrangement to an o-allylphenol, acetylation of the phenolic hydroxyl group, addition of halogen to the allylic double bond, and cyclization in an alkaline alcoholic medium. L. Claisen, Ann., 418, 69 (1919) and Ber., 53, 322 (1920). That approach has been successfully utilized to convert 7-hydroxycoumarins to α-methylfurocoumarins, K. D. Kaufman, *J. ORG. CHEM.*, 26, 117 (1961) and U.S. Pat. No. 3,201,421, including 4,5',8-trimethylpsoralen which was obtained from 4,8-dimethyl-7-hydroxycoumarin in 28% overall yield. Trimethylpsoralen, under the generic name Trioxsalen, has been extensively used with ultraviolet radiation in the treatment of vitiligo, T. B. Fitzpatrick, J. A. Parrish, and M. A. Pathak, in "Sunlight and Man", University of Tokyo Press, Tokyo, Japan, 1974, p. 783–791, and has been recommended in psoriasis therapy, S. W. Becker, *Aust. J. Derm.*, 18, 15–19 (1977). Thus a convenient and efficient synthesis of α-loweralkylfurocoumarins is of contemporary practical interest.

OBJECTS OF THE INVENTION

It is an object of the invention to provide an improved process for making α-loweralkylfurocoumarins. It is a further object of the invention to provide novel compounds useful as intermediates in the preparation of α-loweralkylfurocoumarins. It is another object of the invention to provide novel processes for the production of such intermediates. It is an additional object of the invention to avoid the disadvantages of the prior art and to obtain such advantages which will appear as the description proceeds.

BRIEF DESCRIPTION OF THE INVENTION

The invention relates to a process which comprises providing a 7-(2'-halo-loweralk-2'-enyloxy)coumarin having an active hydrogen in the ortho position and heating it, preferably but not necessarily, in a basic tertiary amine solvent, for a time and at a temperature such that a Claisen rearrangement is effected. The heating is continued at least until the predominant product is the intermediate (2'-halo-loweralk-2'-enyl)-7-hydroxycoumarin, preferably until the predominant product is the α-loweralkylfurocoumarin, and the reaction is most advantageously conducted without isolation of the intermediate product. Advantageously, the reaction may include the step of heating, preferably in the presence of a hydrogen halide acceptor, a 1,2-dihalo-loweralk-2-ene with a 7-hydroxycoumarin having an active hydrogen in the ortho position, to provide starting material.

The Claisen rearrangement of β-haloallyl ethers is of a type known in the art as "abnormal", D. S. Tarbell, *Org. Reactions*, 2, 10 (1944). These abnormal rearrangements usually proceed in poor yield. Thus, the rearrangement of β-bromoallyl phenyl ether has been reported to proceed in 30% yield in boiling decalin. [J. von Braun, Ann., 449, 264, (1926)]. However, Hurd and Webb [C. D. Hurd and C. N. Webb, *J. Amer. Chem. Soc.*, 58, 2190 (1926)] were unable to obtain a pure product from the same rearrangement in decalin or fluorene or by heating without a solvent, but isolated minor amounts of the phenol and the cyclized product α-methylbenzofuran from the Claisen rearrangement of β-chloroallyl phenyl ether. It is therefore surprising that, in the process of the invention, there are obtained high yields both of (2'-halo-loweralk-2'-enyl)-7-hydroxycoumarin and α-loweralkylfurocoumarin. This is even more surprising in view of the fact that Anderson et al., *JCS Chem. Comm.*, 1974, p. 174, was unable to obtain any cyclized product from chloroallyl phenyl ethers after 48 hours in boiling N,N-diethylaniline. To obtain a cyclized product, namely, a 2-methylbenzo [b] furan, it was necessary for Anderson et al. to treat the ortho-chloroallyl phenol under acidic conditions in a separate step. Thus, the discovery that 7-(2'-halo-loweralk-2'-enyloxy)coumarins can be converted directly to α-loweralkylfurocoumarins, in the presence of an acid-binding agent, and especially most conveniently by boiling in N,N-diloweralkylaniline or like basic solvent, is entirely unexpected.

The invention is particularly directed to the preparation of trimethylpsoralen and analogues thereof from a (2'-halo-loweralk-2'-enyl)-7-hydroxycoumarin having a reactive hydrogen in the 6-position and a substituent in the 8-position effective to block the formation of isopsoralenes. In this process, both the starting compound, that is, a 7-(2'-halo-loweralk-2'-enyloxy)coumarin having an active hydrogen in the 6-position and a blocking group in the 8-position and the 6-(2'-halo-loweralk-2'-enyl)-7-hydroxycoumarin are novel intermediates which are readily converted to the corresponding psoralene compounds on heating in a N,N-diloweralkylaniline or like tertiary amine solvent for a time and at a temperature such that rearrangement and cyclization is effected.

The isopsoralenes are prepared in a like manner from 7-(2'-halo-loweralk-2'-enyloxy)coumarins having an active hydrogen in the 8-position. The starting ether for this conversion was prepared by Shamshurin et al., Trudy Uzbekskogo Gosudarst Univ. (N.S.), No. 25, Khim., No. 1, 1–8 (1941), but its conversion either to a (2'-halo-loweralk-2'-enyl)-7-hydroxycoumarin or to an α-loweralkylfurocoumarin has not been reported.

The process of the invention may be illustrated by the following flow diagram:

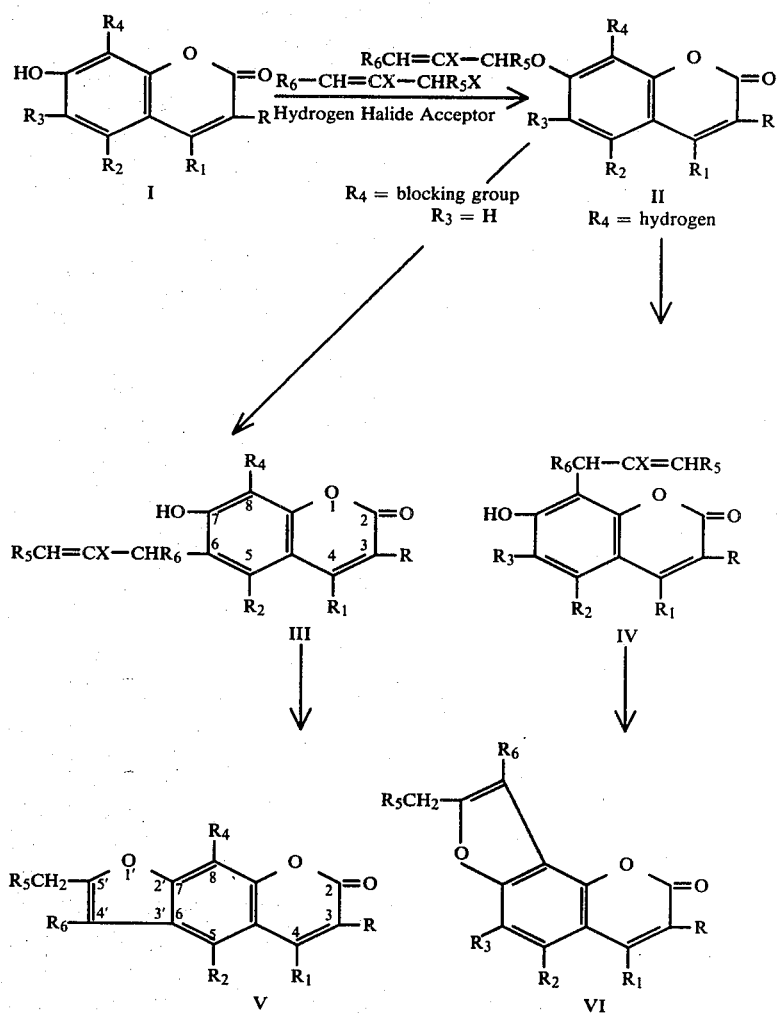

In Formula I, R, $R_1$, $R_2$, $R_3$, and $R_4$ can be hydrogen, alkyl, and lower-alkoxy, provided at least one of $R_3$ and $R_4$ is hydrogen. In Formula II, additionally, $R_5$ and $R_6$ can be hydrogen or lower-alkyl. In Formula III, $R_4$ must be a blocking group, that is, other than hydrogen and, for the conversion to compound IV, the $R_4$ must be hydrogen, in which case $R_3$ can be hydrogen also. The X is halogen, advantageously, chlorine or bromine. Compounds I, V, and VI are known compounds, as is compound II where $R_1$ is methyl and all of the other R's are hydrogen. Compounds III and IV are novel intermediates useful in the production of compounds V and VI, and compound II, except for the case noted above, is a novel compound useful as an intermediate in the production of compounds III and V.

Suitable known starting compounds of Formula I include:
7-hydroxycoumarin,
7-hydroxy-4-methylcoumarin,
7-hydroxy-8-methylcoumarin,
7-hydroxy-4,8-dimethylcoumarin,
7-hydroxy-3,6-diethyl-4-methylcoumarin,
7-hydroxy-4-methyl-6-octadecylcoumarin,
7-hydroxy-3,4,5-trimethyl-8-propylcoumarin,
7-hydroxy-5-methoxy-4-methylcoumarin,
7-hydroxy-8-methoxycoumarin, and
7-hydroxy-8-methoxy-4-methylcoumarin.

Representative examples of known 1,2-dihalo-lower-alkenes suitable for use in the process include:
2,3-dichloropropene,
2,3-dibromopropene,
2,3-dichloro-1-pentene,
1,2-dichloro-2-pentene,
3,4-dibromo-2-pentene,
2,3-dichloro-1-butene,
1,2-dichloro-2-butene,
1,2-dibromo-2-decene,
2,3-dibromo-1-hexene,
1,2-dibromo-2-hexene,
3,4-dibromo-6-methyl-2-heptene, and
3,4-dibromo-2-nonene.

Representative examples of compounds II (flow diagram on page 4) which can be prepared from the foregoing or similar known starting materials, are as follows:
4,8-dimethyl-7-(2'-bromoallyloxy)coumarin,
4,8-dimethyl-7-(2'-chloroallyloxy)coumarin,
4-methyl-7-(2'-bromoallyloxy)coumarin,
7-(1'-ethyl-2'-chloroallyloxy)coumarin,
7-(1'-methyl-2'-bromobut-2'-enyloxy)-3,4,5-trimethyl-8-propylcoumarin,
7-(1'-isobutyl-2'-bromobut-2'-enyloxy)-4-methyl-6-octadecylcoumarin,
7-(2'-bromodec-2'-enyloxy)-8-methoxycoumarin, 7-(2'-bromoallyloxy)-8-methoxycoumarin,
7-(2'-chloroallyloxy)coumarin,
7-(2'-chloropent-2'-enyloxy)-4,8-dimethylcoumarin, and
7-(2'-bromoallyloxy)-8-methylcoumarin.

Representative examples of compounds III (flow diagram) which can be prepared by the abnormal Claisen reaction from the foregoing and similar starting materials, are as follows:

6-(2'-chloroallyl)-4,8-dimethyl-7-hydroxycoumarin,
6-(2'-bromoallyl)-4,8-dimethyl-7-hydroxycoumarin,
6-(2'-bromoallyl)-7-hydroxy-8-methoxycoumarin,
6-(1'-ethyl-2'-chloroallyl)-4,8-dimethyl-7-hydroxycoumarin,
6-(1'-methyl-2'-bromobut-2'-enyl)-7-hydroxy-3,4,5-trimethyl-8-propylcoumarin,
6-(2'-bromoallyl)-7-hydroxy-8-methylcoumarin, and
6-(1'-heptyl-2'-bromoallyl)-7-hydroxy-8-methoxycoumarin.

Representative examples of compounds IV (flow diagram) which can be made from the foregoing and similar starting materials are as follows:

8-(2'-bromoallyl)-7-hydroxy-4-methylcoumarin,
8-(2'-chloroallyl)-7-hydroxycoumarin,
8-(2'-chloropent-2'-enyl)-7-hydroxycoumarin, and
8-(2'-bromo-1',5'-dimethylhex-2'-enyl)-7-hydroxy-6-octadecylcoumarin.

Representative examples of compounds V (flow diagram) which can be made by cyclization from the examples of compounds III listed in the foregoing are:

4,5',8-trimethylpsoralen,
5'-methyl-8-methoxypsoralen,
4'-ethyl-4,5',8-trimethylpsoralen,
5'-ethyl-3,4,4'5-tetramethyl-8-propylpsoralen,
5',8-dimethylpsoralen, and
4'-heptyl-8-methoxy-5'-methylpsoralen.

Representative examples of compounds VI (flow diagram) which can be made by cyclization from the examples of compounds IV listed in the foregoing are:

4,5'-dimethylisopsoralen,
5'-methylisopsoralen,
5'-propylisopsoralen, and
5'-isopentyl-6-octadecyl-4'-methylisopsoralen.

The solvent employed for the reaction is not critical; in fact, a fusion process may be used if desired. An acid-binding agent, e.g., a hydrogen halide acceptor, is generally employed in the cyclization step of the invention, i.e., Compound III→V or IV→VI. The solvent in said cyclization reaction preferably comprises or consists of a tertiary amine which is itself a hydrogen halide acceptor. Preferred such tertiary amines are N,N-diloweralkylanilines. The temperature of heating is not critical but should not be so high as to produce undesirable side effects or so low that the reaction proceeds at an uneconomically slow rate. Solvents having boiling points of 190° C. or higher are therefore preferred, and the boiling points of such solvents are generally satisfactory for carrying out the reaction. Atmospheric pressure is ordinarily employed, but increased pressures may be used to permit efficient use of lower-boiling solvents. Likewise, reduced pressures may be employed to permit efficient use of higher-boiling solvents, all as will be apparent to one skilled in the art.

Representative solvents for Step 1 (II→III or IV (flow diagram) are as follows:
 a. No solvent is required. Many Claisen rearrangements carried out without a solvent, i.e., by simply heating a compound of Formula II at ca. 200° C. (at which temperature it melts).
 b. decalin
 c. fluorene
 d. diphenyl ether
 e. diethyleneglycol monoethyl ether
 f. ethyl benzoate
 g. butyl ether
 h. 1,2,4-trichlorobenzene
 i. p-tolunitrile In general, any conventional organic solvent which is non-reactive with the reactants and reaction products under conditions of the reaction may be employed, when a solvent is utilized, as will be apparent to one skilled in the art.

Representative acid-binding agents for Step 2 (III→V or IV→VI (flow diagram) are as follows:

A. Representative solids which can be used in conjunction with solvents a through d above are:
 a. potassium or sodium carbonate
 b. calcium oxide
 c. barium hydroxide
 d. potassium or sodium bicarbonate
 e. potassium or sodium acetate B. Representative basic solvents which can be substituted for or used in conjunction with those solvents a through d in the foregoing are as follows:
 a. N,N-dimethylaniline
 b. N,N-diethylaniline (or other N,N-diloweralkylaniline)
 c. p-toluidine
 d. collidine
 e. tributylamine
 f. N,N-dimethylmesidine
 g. morpholine
 h. 2,4-lutidine
 i. quinoline
 j. methylpiperazine
 k. methylpiperidine Basic solvents of this type are especially preferred when it is desired to proceed directly from Compound II to Compound V or from Compound II to Compound VI without isolation of an intermediate.

DETAILED DESCRIPTION OF THE INVENTION

The following Preparations and Examples are given by way of illustration only, and are not to be construed as limiting.

EXAMPLE I: Preparation of 4,5',8-Trimethylpsoralene

Part 1-A: 4,8-Dimethyl-7-(2'-bromoallyloxy)coumarin

A mixture of 4,8-dimethyl-7-hydroxycoumarin (2.00 g., 10.5 m mole), anhydrous potassium carbonate (2.9 g., 21 m mole), freshly-distilled 2,3-dibromopropene (2.50 g., 12.6 m mole, b.p. 42°–44° C./11 torr), and acetone (75 ml.) was stirred and heated under reflux for six hours. Inorganic salts were filtered from the cooled solution and washed with acetone. Evaporation of the combined filtrate and washing under reduced pressure left a nearly colorless residue (3.52 g., m.p. 128.5°–131° C.) of 4,8-dimethyl-7-(2'-bromoallyloxy)coumarin, that smelled faintly of 2,3-dibromopropene. Recrystallization of a sample (1.00 g.) from methanol gave colorless needles (0.84 g., 91% yield) of m.p. 130°–132° C. Another recrystallization gave an analytical sample of m.p. 131°–131.5° C.

Anal. Calcd. for $C_{14}H_{13}O_3Br$: C, 54.39; H, 4.24; Br, 25.85. Found: C, 54.32; H, 4.24; Br, 26.07.

Part 1-B: 4,5',8-Trimethylpsoralene

A mixture of 4,8-dimethyl-7-(2'-bromoallyloxy)-coumarin (200 mg., 0.65 m mole, m.p. 130°–132° C.) and freshly-distilled N,N-diethylaniline (5.0 ml.) was stirred under a nitrogen atmosphere and heated under reflux for twenty-four hours at an oil bath temperature of 225°±2° C. An ether solution of the dark-brown reaction mixture was filtered, and the filtrate was washed with several portions of 5% aq. sodium hydroxide and one portion of 6 M hydrochloric acid. After drying (MgSO$_4$), the ether solution was concentrated under reduced pressure to a tan residue (131 mg., 88% yield, m.p. 222°–228° C.). Recrystallization of 120 mg. from 95% ethanol gave 4,5',8-trimethylpsoralene as fine needles (82 mg., 60% yield) of m.p. 232.5°–233.5° C. (rptd.: m.p. 234° C.). The melting point of a commercial sample was 230°–232° C. when determined simultaneously. The infrared spectra of the two samples were identical.

EXAMPLE II Preparation of
4,5',8-Trimethylpsoralene

Part 2-A: 4,8-Dimethyl-7-(2'-chloroallyloxy)coumarin

A mixture of 4,8-dimethyl-7-hydroxycoumarin (8.00 g., 42.1 m mole); anhydrous potassium carbonate (18.1 g., 130 m mole); 2,3-dichloropropene (33.6 g., 302 m mole); and acetone (600 ml.) was stirred and heated under reflux for twenty-four hours. The reaction mixture was concentrated to ca. 200 ml., filtered, and the inorganic salts were washed with acetone. Evaporation of the combined filtrate and washing under reduced pressure left a tan-colored residue (11.30 g.). Recrystallization from aqueous methanol gave a 77% yield of 4,8-dimethyl-7-(2'-chloroallyloxy)coumarin as small, off-white needles (8.55 g., m.p. 117.5°–120° C.). Another recrystallization did not change the m.p. but gave an analytical sample.

Anal. Calcd. for $C_{14}H_{13}O_3Cl$: C, 63.52; H, 4.95; Cl, 13.39. Found: C, 63.39; H, 5.12; Cl, 13.52.

Part 2-B: 4,5',8-Trimethylpsoralene

A mixture of 4,8-dimethyl-7-(2'-chloroallyloxy)-coumarin (500 mg., 1.89 m mole) and N,N-diethylaniline (5.0 ml) was protected by an "Aquasorb" (TM), brand of phosphorous pentoxide drying tube, while being heated under reflux for twenty-four hours at an oil bath temperature of 220°–225° C. Treatment of the reaction mixture as described in part 1-B gave some black, ether-insoluble material which was discarded. The desired 4,5',8-trimethylpsoralene was obtained as a tan solid (154 mg., 41.6% yield), which was recrystallized from 95% ethanol to obtain light tan needles (53 mg., 14% yield) of m.p. 233° C. (rptd: m.p. 234° C.). Its infrared spectrum was identical to that of a commercial sample.

EXAMPLE III-Preparation of
4,8-Dimethyl-6-(2'-bromoallyl)-7-hydroxycoumarin

A mixture of 4,8-dimethyl-7-(2'-bromoallyloxy)-coumarin (1.00 g., 3.24 m mole) and freshly distilled N,N-diethylaniline (5.0 ml.) was protected by an "Aquasorb" (TM) tube while being stirred and heated under reflux for three hours at an oil bath temperature of 225°±3° C. An ether solution of the dark brown reaction mixture was filtered to remove a black solid (ca. 10 mg.), extracted with several portions of 5% aqueous sodium hydroxide, washed several times with 6 M hydrochloric acid, dried (MgSO$_4$), and concentrated to a tan solid (0.43 g., m.p. 114°–125° C.) which was probably impure starting material. The alkaline extracts were acidified with concentrated hydrochloric acid to obtain 4,8-dimethyl-6-(2'-bromoallyl)-7-hydroxycoumarin as an off-white solid (0.53 g., 53% yield, m.p. 154°–161° C.) that was collected by ether extraction. Recrystallization from aqueous ethanol, followed by another recrystallization from benzene, gave an analytical sample of m.p. 175°–176° C.

Anal. Calcd. for $C_{14}H_{13}O_3Br$: C, 54.39; H, 4.24; Br, 25.85. Found: C, 54.83; H, 4.39; Br, 25.87

Heating the 4,8-dimethyl-6-(2'-bromoallyl)-7-hydroxycoumarin in the presence of a hydrogen halide acceptor, for example, N,N-dimethylaniline or sym-collidine, converts it to 4,5',8-trimethylpsoralene.

EXAMPLE IV-Preparation of
4,8-Dimethyl-6-(2'-chloroallyl)-7-hydroxycoumarin

A mixture of 4,8-dimethyl-7-(2'-chloroallyloxy)-coumarin (500 mg., 1.89 m mole) and N,N-diethylaniline (5.0 ml.) was protected by an "Aquasorb" (TM) tube while refluxing for nineteen hours at an oil bath temperature of 220°–225° C. The cooled mixture was treated as described in Example III to obtain 4,8-dimethyl-6-(2'-chloroallyl)-7-hydroxycoumarin as a tan solid (307 mg., 61% yield, m.p. 135°–163° C.) from the acidified alkaline extracts. Recrystallization from benzene using active carbon gave small yellow needles (183 mg., 37% yield, m.p. 172°–176° C.).

Anal. Calcd. for $C_{14}H_{13}O_3Cl$: C, 63.52; H, 4.95; Cl, 13.39. Found: C, 63.62; H, 4.75; Cl, 13.42.

Heating the 4,8-dimethyl-6-(2'-chloroallyl)-7-hydroxycoumarin in the presence of a hydrogen halide acceptor, for example, N,N-dimethylaniline or sym-collidine, converts it to 4,5',8-trimethylpsoralene.

EXAMPLE V-Preparation of
4,5'-Dimethylisopsoralene

Part 1-A: 4-Methyl-7-(2'-bromoallyloxy)coumarin

4-Methyl-7-hydroxycoumarin (2.00 g., 11.4 m mole) was refluxed with freshly-distilled 2,3-dibromopropene (2.72 g., 13.6 m mole), anhydrous potassium carbonate (3.15 g., 22.8 m mole), and acetone (80 ml.) for four hours. The reaction mixture was treated as described for the preparation of Example I, Part 1-A to obtain 4-methyl-7-(2'-bromoallyloxy) coumarin as an off-white solid (3.70 g.) that contained some excess 2,3-dibromopropene. Recrystallization of a portion (500 mg.) from ligroin (b.p. 100°–120° C.) gave needles (394 mg., 89% yield) of m.p. 109.5°–110.5° C. An analytical sample of m.p. 110°–111° C. was obtained by recrystallization from methanol.

Anal. Calcd. for $C_{13}H_{11}O_3Br$: C, 52.97; H, 3.75; Br, 27.08. Found: C, 52.98; H, 3.80; Br, 27.18.

Part 1-B: 4,5'-Dimethylisopsoralene

Rearrangement and cyclization of 4-methyl-7-(2'-bromoallyloxy)coumarin (500 mg., 1.69 m mole) was carried out as described in Example I, Part 1-B, except that N,N-dimethylaniline (12.5 ml.) was used instead of the diethyl homolog. The same purification procedure gave 4,5'-dimethylisopsoralene as a tan solid (289 mg., 80% yield) of m.p. 173°–179.5° C. Recrystallization from methanol using active carbon afforded light tan needles (161 mg., 45% yield) of m.p. 182.5°–184° C. (rptd.: m.p. 182°–183° C.). The infrared spectra of this sample and that of an authentic sample were identical.

EXAMPLE VI-Preparation of 4-Methyl-8-(2'-bromoallyl)-7-hydroxycoumarin

A mixture of 4-methyl-7-(2'-bromoallyloxy)coumarin (500 mg.) and freshly-distilled N,N-diethylaniline (12.5 ml.) was stirred under a nitrogen atmosphere and heated under reflux for five hours at an oil bath temperature of ca. 225° C. An ether solution of the reaction mixture was extracted with several portions of 5% aqueous sodium hydroxide, which were acidified and re-extracted with ether to obtain 4-methyl-8-(2'-bromoallyl)-7-hydroxycoumarin as an off-white solid (206 mg.). Recrystallization from 95% ethanol gave fine, off-white needles (102 mg., 20% yield) of m.p. 201°–202° C. Another recrystallization gave an analytical sample of m.p. 204.5°–205° C.

Anal. Calcd. for $C_{13}H_{11}O_3Br$: C, 52.97; H, 3.75; Br, 27.08 Found: C, 52.97; H, 3.75; Br, 26.56.

Heating the 4-methyl-8-(2'-bromoallyl)-7-hydroxycoumarin in the presence of a hydrogen halide acceptor, for example, N,N-dimethylaniline or sym-collidine, converts it to 4,5'-dimethylisopsoralene.

EXAMPLES VII THROUGH XVI-Additional Preparations

In the same manner as given in the foregoing examples, by the reaction of starting compounds having Formula I with selected 1,2-dihaloloweralkenes, additional compounds having Formula II are produced and converted to end products having Formulas V and VI, preferably without isolation of the intermediate compounds of Formulas III and IV, respectively, all according to the reaction sequence fully set forth hereof and employing, as starting materials of Formula I, those compounds set forth hereof; as reactant 1,2-dihaloloweralkenes, those compounds set forth hereof; thus to prepare compounds of Formula II as set forth hereof, as well as compounds of Formula III as set forth hereof, and compounds of Formula IV as set forth hereof, which latter type of compounds of Formulas III and IV are preferably not isolated, but converted directly in situ, according to the foregoing examples, to the end products being compounds of Formulas V and VI, also as set forth hereof. The procedure employed is substantially as set forth in the foregoing example, as well as reaction conditions and work-up for procurement of the final end products in each case. The end products in each case are the compounds of Formulas V and VI set forth hereof.

As used herein, loweralkyl means such radicals containing up to and including eight carbon atoms, such as methyl, ethyl, propyl, butyl, amyl, hexyl, heptyl and octyl, and loweralkoxy means such radicals of the formula -O-loweralkyl.

It is to be understood that the invention is not to be limited to the exact details of operation or structure shown and described, as obvious modifications and equivalents will be apparent to one skilled in the art.

I claim:

1. A compound of the formula

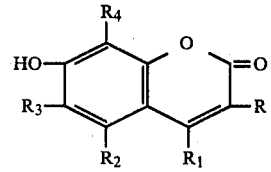

in which R, $R_1$, and $R_2$ are selected from the group consisting of hydrogen, lower-alkyl, and lower-alkoxy; $R_4$ is lower-alkyl or lower-alkoxy, and $R_3$ is $R_5$-CH=CX-CHR$_6$-, in which $R_5$ and $R_6$ are hydrogen or lower-alkyl and X is bromine or chlorine.

2. The compound of claim 1, in which $R_1$ and $R_4$ are methyl and R and $R_2$ are hydrogen.

3. The compound of claim 2, wherein X is bromine.

4. The compound of claim 2, wherein X is chlorine.

5. The compound of claim 2, wherein $R_5$ and $R_6$ are both hydrogen.

6. The compound of claim 1 which is 4,8-dimethyl-6-(2'-bromoallyl)-7-hydroxycoumarin.

7. The compound of claim 1 which is 4,8-dimethyl-6-(2'-chloroallyl)-7-hydroxycoumarin.

8. A compound of the formula

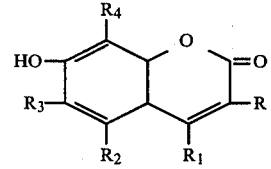

in which R, $R_1$, and $R_2$ are selected from the group consisting of hydrogen, lower-alkyl, and lower-alkoxy; $R_3$ is hydrogen, lower-alkyl, or lower-alkoxy, and $R_4$ is $R_5$-CH=CX-CHR$_6$-, in which $R_5$ and $R_6$ are hydrogen or lower-alkyl and X is bromine or chlorine.

9. The compound of claim 8, in which $R_1$ is methyl and R, $R_2$ and $R_3$ are hydrogen.

10. The compound of claim 9, wherein X is bromine.

11. The compound of claim 9, wherein $R_5$ and $R_6$ are both hydrogen.

12. The compound of claim 8 which is 4-methyl-8-(2'-bromoallyl)-7-hydroxycoumarin.

* * * * *

UNITED STATES PATENT AND TRADEMARK OFFICE
CERTIFICATE OF CORRECTION

PATENT NO. : 4,235,781          Page 1 of 2
DATED : November 25, 1980
INVENTOR(S) : Kurt D. Kaufman It is certified that error appears in the above-identified patent and that said Letters Patent are hereby corrected as shown below:

[57], lines 2 & 3; "hydrox-ycoumarin" should be hyphenated -- hydroxy-coumarin --
Col. 1, lines 26 & 27; "Trime-thylpsoralen," should be hyphenated -- Tri-methylpsoralen, --
Col. 2, lines 22 & 23; "-7-hydrox-ycoumarin" should be hyphenated -- -7-hydroxy-coumarin --
Col. 2, lines 44 & 45; "isop-soralenes." should be hyphenated -- iso-psoralenes. --
Col. 2, lines 53 & 54; "N,N-diloweralk-ylaniline" should be hyphenated -- N,N-diloweralkyl-aniline --
Col. 4, line 57; delete "on page 4"
Col. 4, lines 64 & 65; "-trimeth-yl-8-" should be hyphenated -- -trimethyl-8- --
Col. 5, lines 13 & 14; "-7-hydrox-ycoumarin," should be hyphenated -- -7-hydroxy-coumarin, --
Col. 5, lines 18 & 19; "-8-methox-ycoumarin." should be hyphenated -- -8-methoxy-coumarin. --
Col. 5, line 65; delete "(" preceding "II"
Col. 6, line 16; delete "(" preceding "III"

UNITED STATES PATENT AND TRADEMARK OFFICE
CERTIFICATE OF CORRECTION

PATENT NO. : 4,235,781
DATED : November 25, 1980
INVENTOR(S) : Kurt D. Kaufman

It is certified that error appears in the above-identified patent and that said Letters Patent are hereby corrected as shown below:

Col. 8, lines 16 & 17 and 37 & 38; "-7-hydrox-ycoumarin" should be hyphenated -- -7-hydroxy-coumarin --

Col. 9, lines 25 & 26; "-7-hydrox-ycoumarin" should be hyphenated -- -7-hydroxy-coumarin --

Signed and Sealed this

Tenth Day of March 1981

[SEAL]

Attest:

RENE D. TEGTMEYER

Attesting Officer  Acting Commissioner of Patents and Trademarks